(12) United States Patent
Goudaliez et al.

(10) Patent No.: US 7,048,709 B2
(45) Date of Patent: May 23, 2006

(54) BAG PROVIDED WITH MEANS FOR THE TEMPORARY ASSOCIATION OF A FILTER

(75) Inventors: Francis Goudaliez, Faches-Thumesnil (FR); Thierry Verpoort, Mouvaux (FR); Gus Ribeiro, Sydney (AU)

(73) Assignee: MacoPharma, Mouvaux (FR)

( * ) Notice: Subject to any disclaimer, the term of this patent is extended or adjusted under 35 U.S.C. 154(b) by 289 days.

(21) Appl. No.: 10/167,995

(22) Filed: Jun. 12, 2002

(65) Prior Publication Data

US 2003/0004453 A1 Jan. 2, 2003

(30) Foreign Application Priority Data

Jun. 12, 2001 (FR) .................................. 01 07679

(51) Int. Cl.
*A61M 35/00* (2006.01)
*A61B 19/00* (2006.01)
*B65D 30/22* (2006.01)
*B04B 5/10* (2006.01)
*C02F 1/38* (2006.01)

(52) U.S. Cl. ................... 604/6.09; 604/4.01; 604/6.16; 604/408; 604/410; 383/40; 128/DIG. 24; 210/360.1; 210/782; 494/36; 494/37

(58) Field of Classification Search ............... 604/4.01, 604/6.01–6.04, 6.15, 6.16, 6.09, 411–415, 604/403, 406, 408–410, 903; 128/DIG. 24; 494/36, 37; 206/828; 222/206, 211–2; 435/2; 210/767, 780–2, 252, 257.1, 257.2, 348, 210/294–7, 359, 360.1–360.2
See application file for complete search history.

(56) References Cited

U.S. PATENT DOCUMENTS 3,986,506 A * 10/1976 Garber et al. ............... 604/406

(Continued)

FOREIGN PATENT DOCUMENTS

NL 1966731 9/1969

OTHER PUBLICATIONS

European Patent Application No. EP0976413A1, Francis Goudaliez, "Ensemble de Poches en circuit clos, destinéa Recueillir, Séparer et Purifier les Différents Constituants du Sang á Partir d'un Prélévement de Sang Total", European Patent Office, Jul. 23, 1999.

(Continued)

*Primary Examiner*—Patricia Bianco
(74) *Attorney, Agent, or Firm*—Baker Botts L.L.P.; Paul R. Morico (57) ABSTRACT

The disclosure includes a flexible bag (1) intended to receive a biological fluid with a view to its centrifugation. The bag includes an external enclosure (2) formed by two sheets of flexible plastic (3, 3') connected at their periphery (4) so as to define an internal volume (5) for the fluid. The external enclosure (2) is provided with at least one inlet (6) and/or outlet (7) orifice for the fluid. The bag (1) also includes means (8) for the temporary association of at least one component with the bag (1). The means (8) is disposed on the external enclosure (2), in which the temporary association means are assembled on the bag (1) on a part of the periphery (4) of the enclosure (2) and are arranged to allow the insertion of the component between the means (8) and the enclosure (2) so as to provide temporary association during the centrifugation of the bag (1).

13 Claims, 5 Drawing Sheets

U.S. PATENT DOCUMENTS

| | | | |
|---|---|---|---|
| 4,596,657 A | 6/1986 | Wisdom | 210/206 |
| 4,701,267 A | 10/1987 | Watanabe et al. | 210/806 |
| 4,735,613 A * | 4/1988 | Bellin et al. | 604/141 |
| 4,767,541 A | 8/1988 | Wisdom | 210/749 |
| 4,919,823 A | 4/1990 | Wisdom | 210/749 |
| 4,925,572 A | 5/1990 | Pall | 210/767 |
| 4,985,153 A | 1/1991 | Kuroda et al. | 210/782 |
| 5,234,593 A | 8/1993 | Kuroki et al. | 210/496 |
| 5,269,946 A | 12/1993 | Goldhaber et al. | 210/767 |
| 5,478,470 A | 12/1995 | Fukuda et al. | 210/500.1 |
| 5,665,233 A | 9/1997 | Fukuda et al. | 210/483 |
| 5,836,934 A * | 11/1998 | Beshel | 604/410 |
| 6,123,859 A | 9/2000 | Lee et al. | 210/767 |
| 6,197,207 B1 | 3/2001 | Chapman et al. | 210/767 |

OTHER PUBLICATIONS

European Patent Application No. 0426475A1, Raymond P. Goodrich, Jr., "Blood Bag for Lyophillization and Method of Use", European Patent Office, Nov. 1, 1990.

German Patent Application No. DE 3906418A1, Fuchs, J., "Enteralie Emährungsanordnung und Verfahren zur Herstellung Elner Enteral Einsetzbaren Ernährungsanordnung", Sep. 13, 1990.

\* cited by examiner

BAG PROVIDED WITH MEANS FOR THE TEMPORARY ASSOCIATION OF A FILTER

CROSS-REFERENCE TO RELATED APPLICATION

This Application claims priority to French Patent Application Ser. No. FR 01/07679 entitled "A Bag Provided with Mean for the Temporary Association of a Filter" filed on Jun. 12, 2001 which is hereby incorporated by reference herein for all purposes.

FIELD OF THE INVENTION

The invention concerns a flexible bag intended to receive a biological fluid, a bag system comprising such a bag, and a method using such a system.

Such a bag is intended in particular to receive blood or a component of blood.

BACKGROUND

The integration of such a bag in a closed system with a view to separating the blood into its components is known, in particular from the document U.S. Pat. No. 4,767,541.

To this end, the system typically comprises means of taking blood, a primary bag intended to collect the blood and, connected to this by means of tubes, at least one filter and at least one secondary bag intended to receive the filtrate.

The use of such a system involves successively a centrifugation step for separating the blood into its various components, namely plasma, white corpuscles or leukocytes, and red corpuscles, and a step of filtration of at least one component of the blood, in order to eliminate the leukocytes. It is in fact known that leukocytes are undesirable in blood components to be transfused.

During the centrifugation step, it is necessary to introduce into the centrifugation bowl not only the various flexible bags but also the filter.

However, it proves that, during this step, the filter may be damaged, because of the acceleration and the centrifugation speed: it may in fact bend, thus creating preferential passages for the blood, or may break, which consequently makes the filtration inoperative.

In addition, and in particular when the filter has a rigid enclosure, the centrifugation thereof conjointly with the flexible bags and the tubes may, through friction, cause damage to these. In some cases, this damage may cause piercing of a bag and/or a tube, which makes the system unusable for the separation of the blood into its components.

To remedy these problems, various systems have already been proposed. These can be classified into two categories:

systems requiring a particular arrangement of the centrifugation bowl, for example by inserting in the bowl a rigid support intended to accept the filter during the centrifugation step and therefore to separate the filter from the other components of the system;
  systems having recourse to means external to the centrifugation bowls, namely, for example, means of associating the filter on the bowl.

The systems in the first category have in particular the drawback of requiring a particular type of support for each centrifugation bowl. In particular, the presence of the rigid support inside the bowl limits the space available for the system.

It is known that it is possible to provide, for the systems in the second category, either association means integrated in the filter or external to it. In the first case, the production of the filter is made more complicated. In the second case, adhesive strips are in particular used which provide unreliable association.

Moreover, it is known from the document U.S. Pat. No. 5,836,934 that a case can be associated on a bag in order to house a filter during the centrifugation. This solution has in particular the drawback of not being simple to implement in that it requires the production of a specific case which must be associated with the bag during a specific step. In addition, the association is effected on one face of the bag which, during filling of the bag, deforms. Thus a loss of reliability of the association may be caused, notably during the high forces which are caused by the centrifugation.

SUMMARY

In order to mitigate these drawbacks, the invention proposes in particular means of temporarily associating the filter on one of the bags in the system, which allow reliable and easy association thereof without substantially increasing the difficulty in production and the cost of the said bag. Thus, during the centrifugation step, the bag and the filter temporarily form a compact assembly which ensures the protection of the various components of the system, in particular avoiding friction between them, as well as the movement of the filter during the centrifugation.

In addition, this assembly is easy to handle, since it can be placed in the centrifugation bowl, then removed once the centrifugation has ended, in a simple and rapid fashion, and without risking mixing the centrifuged components.

In addition, the system can be used with the types of bowl commercially available.

According to a first aspect, the invention concerns a flexible bag intended to receive a biological fluid with a view to its centrifugation, comprising an external enclosure formed by two sheets of flexible plastic connected at their periphery so as to define an internal volume for the said fluid, the said external enclosure being provided with at least one inlet and/or outlet orifice for the fluid, the said bag also comprising means for the temporary association of at least one component with the said bag, the said means being disposed on the external enclosure, in which the temporary association means are assembled on the bag on a part of the periphery of the enclosure and are arranged to allow the insertion of the said component between the said means and the said enclosure so as to provide temporary association during the centrifugation of the bag.

According to one embodiment, the temporary association means are formed from a strip of flexible plastics material, the said strip being assembled on the bag over a part of the periphery of the enclosure so as to form a passage between the said strip and the said enclosure.

According to another embodiment, the temporary association means are formed by a portion of a sheet of flexible plastics material, the said portion being associated with the bag over part of the periphery of the enclosure so as to form a housing between the said portion and the said enclosure.

According to a second aspect, the invention concerns a bag system comprising a bag as described above, in which a filter is connected to the said bag by means of a tube so as to be able to be associated temporarily with the said bag.

According to a third aspect, the subject matter of the invention is a method of separating blood into its various components using a bag system, the said method comprising the steps making provision for:

associating the filter with the bag according to the invention;
  taking off the whole blood in a bag;
  centrifuging the bag system so as to separate the blood into its various components;
  separating the filter from the bag so as to allow subsequent filtration of at least one component of the blood.

BRIEF DESCRIPTION OF THE DRAWINGS

Other objects and advantages of the invention will emerge during the description which follows, with reference to the accompanying drawings, in which.

DETAILED DESCRIPTION

Figure 1A:
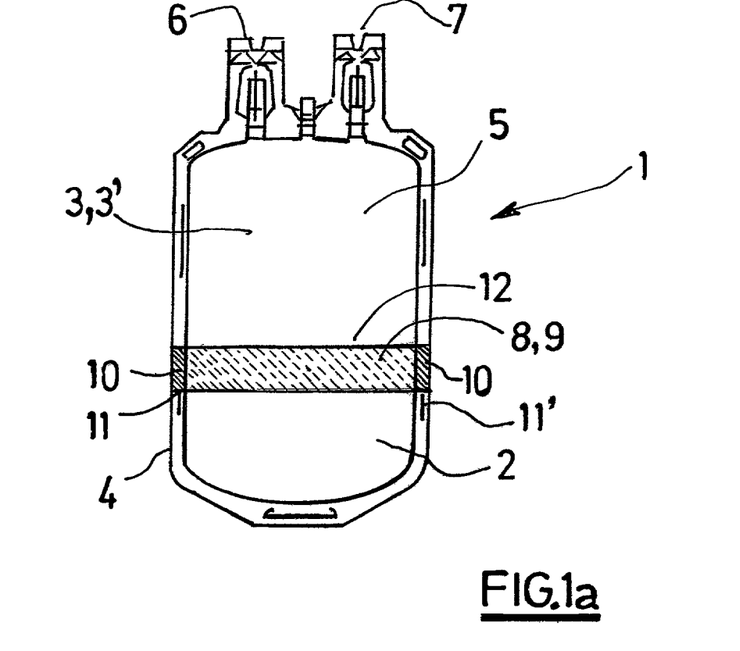
FIG. 1a is a front view of a flexible bag comprising means for the temporary association of the filter, according to a first embodiment.
Figure 1B:
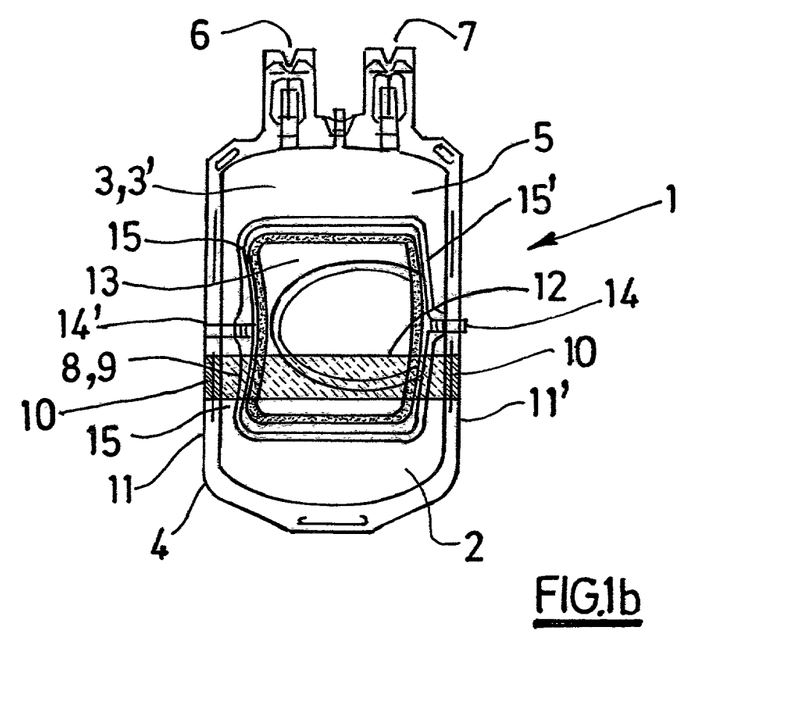
FIG. 1b depicts the bag of FIG. 1 on which a filter is associated, by means of temporary association means.
Figure 2A:
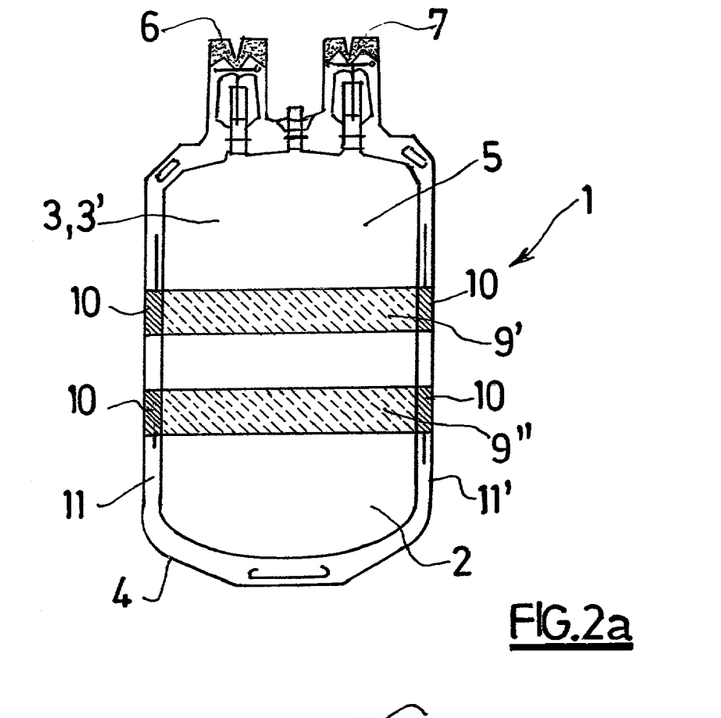
FIG. 2a is a front view of a flexible bag comprising means for the temporary association of the filter, according to a second embodiment.
Figure 2B:
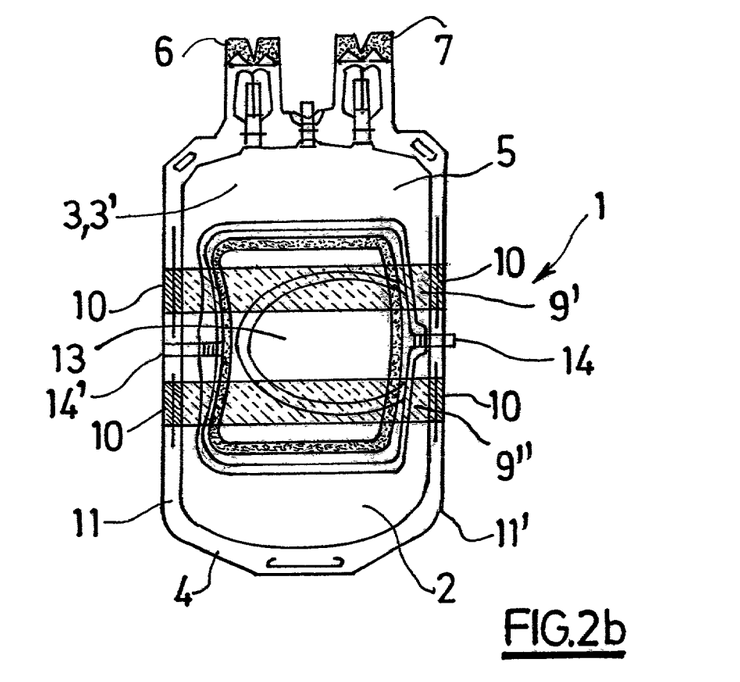
FIG. 2b depicts the bag of FIG. 2a on which a filter is associated, by means of temporary association means.
Figure 3:
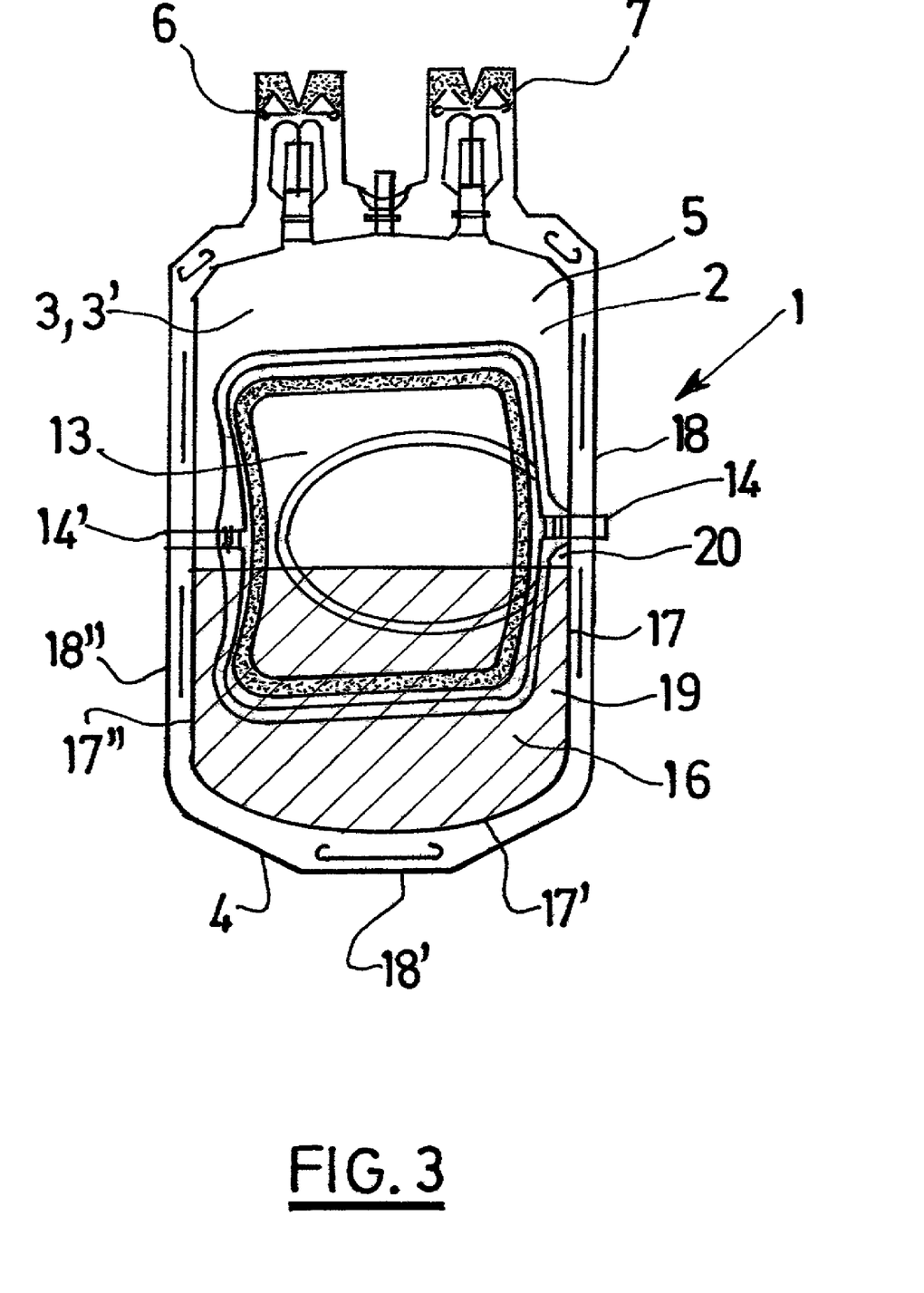
FIG. 3 is a front view of a flexible bag on which a filter is associated by means of temporary association means, according to a third embodiment.

FIGS. 1, 2 and 3 depict a flexible bag 1 intended to receive a biological fluid. In one particular example, this fluid is blood or one of the components of blood.

In the embodiments depicted, the bag 1 is substantially rectangular in shape. It comprises an external enclosure 2 formed by two flexible weldable and sterilisable plastic sheets 3 and 3', for example made from PVC. These two sheets 3 and 3' are connected at their periphery 4, for example by welding, so as to define an internal volume 5 for the fluid.

The flexible bag 1 comprises, on its external enclosure 2, an inlet orifice 6 and an outlet orifice 7 for the fluid. These orifices 6 and 7 are connected to flexible tubes, typically made from plastics material, intended to allow the circulation of the fluid in the system.

According to another embodiment, not shown, the fluid inlet and outlet can take place through one and the same orifice.

The flexible bag 1 also comprises temporary association means 8, enabling at least one other component to be associated with it. These temporary association means 8 are disposed on the external enclosure 2. Thus it is possible to temporarily insert a component between the temporary association means 8 and the external enclosure 2.

In FIGS. 1a and 1b (first embodiment), the temporary association means 8 are formed by a strip of flexible plastics material 9. This strip 9 is assembled, for example by welding, by means of its lateral ends 10, on two opposite edges 11, 11' of the periphery 4 of the bag 1.

An opening 12 is provided between the strip 9 and the external enclosure 2 of the bag 1, so as to allow the temporary manual insertion of the component. The width of the strip 9 is designed so that it is possible to insert the component and to hold it, once inserted, against the external enclosure 2 of the bag 1.

It is thus possible to make the component pass between the strip 9 and the external enclosure 2 of the bag 1, so as to associate it temporarily with the bag 1.

In FIG. 1b, the component associated with the bag 1 is a filter 13. This filter 13, substantially rectangular in shape, is connected to the bag 1 by a tube 14, and to another bag (not shown) by a tube 14'. The two tubes 14 and 14' are placed on two opposite edges 15, 15' of the filter 13, so as to facilitate the insertion of the filter 13 between the strip 9 and the external enclosure 2 of the flexible bag 1.

This type of flexible filter is for example described in the document FR-2 677 883 issuing from the applicant.

In a second embodiment, illustrated in FIGS. 2a and 2b, the temporary association means 8 are formed by two strips of flexible plastics material 9' and 9". These two strips can be identical to that of the first embodiment and are disposed parallel to each other, in order to provide a better holding of the filter 13 on the bag 1.

In this embodiment, the tubes 14 and 14' can be placed between the two strips 9' and 9" in order to improve this holding still further.

FIG. 3 shows a third embodiment of a flexible bag 1 comprising temporary association means 8.

In this embodiment, the temporary association means 8 are formed by a portion of a sheet of flexible plastics material 16. The sheet portion 16 is substantially rectangular in shape. Its surface is approximately half the size of the surface of the sheets 3 and 3' which form the enclosure 2.

The sheet portion 16 is connected by means of three of its sides 17, 17' and 17" to three adjacent edges 18, 18' and 18" of the periphery 4 of the flexible bag 1.

Thus the filter 13 can be inserted temporarily in a housing 19 formed between the sheet portion 16 and the external enclosure 2 of the bag 1, by means of an opening 20.

In the embodiment depicted in FIG. 3, the filter 13 is housed partially in the housing 19, the tubes 14 and 14' thus remaining outside the housing 19.

In the embodiments depicted in FIGS. 1, 2 and 3, the strip of plastics material 9, the strips 9' and 9" and the sheet portion 16 are respectively connected to the bag 1 so that the filter 13, once inserted, is situated substantially at the centre of the bag 1. This central position facilitates the handling of the system, and, during the centrifugation step, allows better distribution of the weights.

In particular, this positioning avoids the filter 13 coming into contact with the bottom of the bowl, which is a source of damage to the filter 13.

The temporary association means 8 can be connected to the bag 1 by welding. To this end, it is advantageous for the sheets 3, 3' and respectively the strip 9, the strips 9', 9" and the sheet portion 16 to be produced from the same plastics material so as to be able, in a single welding step, to produce the bag 1 according to the invention. In addition, the connection of the temporary association means 8 to a part of the periphery 4 of the enclosure 2 allows a particularly reliable association because of the strength and stability of the said periphery.

Figure 4:
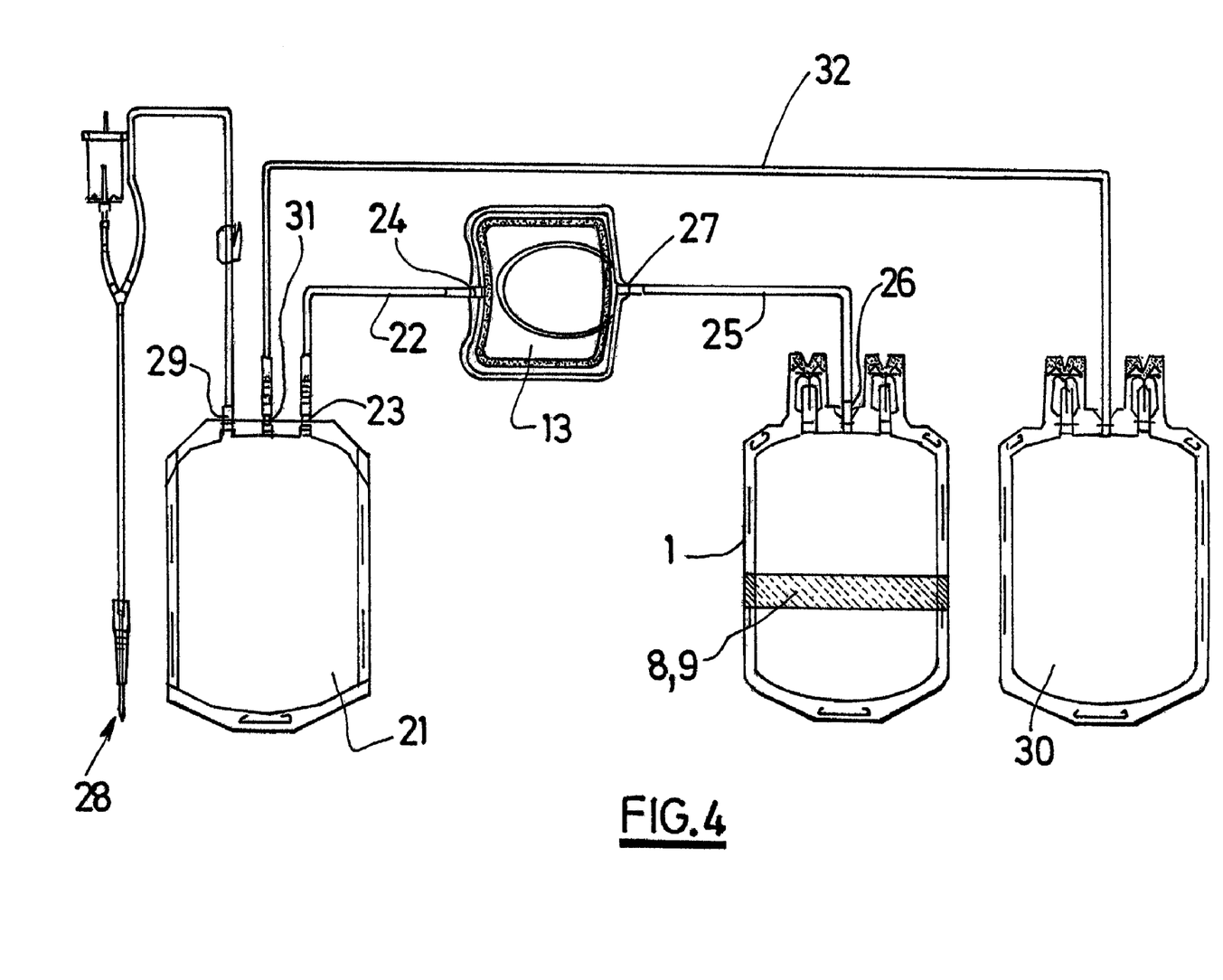
FIG. 4 depicts, in schematic front view, a bag system for the sterile closed-circuit filtration of an erythrocyte concentrate.
Figure 5:
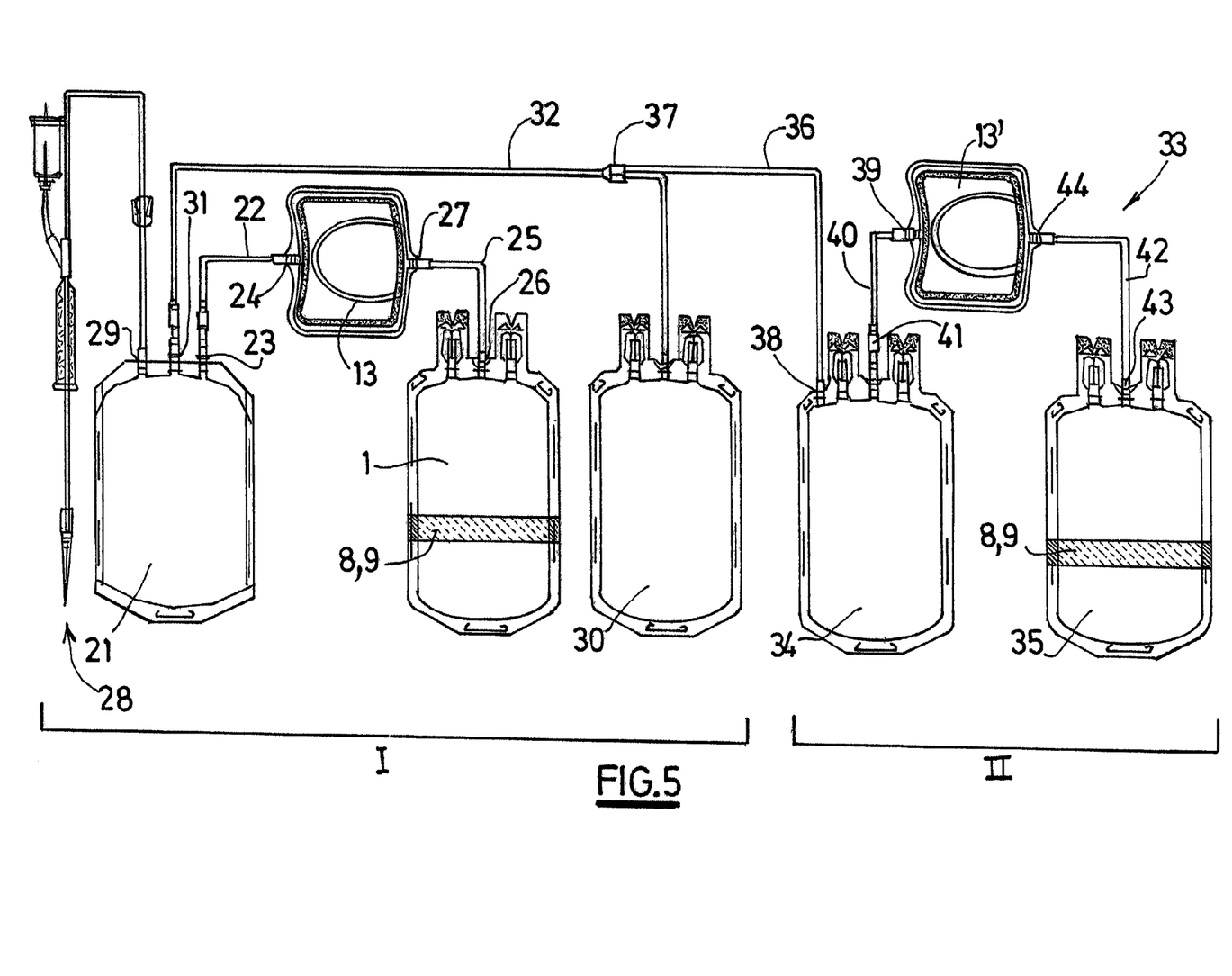
FIG. 5 depicts, in schematic front view, a bag system for the sterile closed-circuit filtration of the plasma and erythrocyte concentrate.

A description is now given, in relation to FIGS. 4 and 5, of a first and second embodiment of a bag system for the sterile closed-circuit filtration of a biological fluid, this system comprising a flexible bag 1 as described above.

The bag system comprises a primary bag 21 intended to contain the blood to be filtered, the said primary bag 21 being connected by means of a first tube 22, and at one of its outlet orifices 23, to the inlet orifice 24 of the filter 13. A bag 1, referred to as secondary bag, intended to receive the filtrate, is connected by means of a second tube 25, and at one of its inlet orifices 26, to the outlet orifice 27 of the filter 13.

The bag 1 comprises temporary association means 8 in the form of a strip of flexible plastics material 9, as described above in relation to the first embodiment.

The bag system depicted in FIG. 4 also comprises means 28 of taking whole blood connected to an inlet orifice 29 of the primary bag 21, and a satellite bag 30 connected to an outlet orifice 31 of the primary bag 21 by means of a third tube 32.

In this embodiment, the bag system is typically intended for the sterile closed-circuit filtration of an erythrocyte concentrate.

This system makes it possible, after having been sterilised, to carry out the following steps in closed circuit:
- associating the filter 13 with the bag 1, referred to as the secondary bag, by means of a strip of flexible plastics material 9 forming a temporary association means 8;
- collecting the whole blood in the primary bag 21 previously filled with an anticoagulant solution;
- centrifuging the system so as to separate the blood into its components;
- separating the filter 13 from the bag 1;
- collecting the high platelet content plasma in the satellite bag 30;
- filtering the erythrocyte concentrate and collecting the filtration in the bag 1 previously filled with a preservation solution.

In a variant, the filter 13 can be associated with the bag 1 subsequently to the collection of the whole blood in the primary bag 21.

In the second embodiment (FIG. 5), the bag system is typically intended for the sterile closed-circuit filtration of the plasma and an erythrocyte concentrate.

This system comprises, in its part I, a bag system like the one described in relation to FIG. 4, intended for the sterile closed-circuit filtration of an erythrocyte concentrate, and also comprises a part II which is connected to the part I by a tube 36 connected to the tube 32 by means of a junction 37.

The part II is formed by an assembly 33 comprising a satellite bag 34, a filter 13' and a satellite bag 35, the assembly 33 being intended for the filtration of the plasma.

The bag 34, intended to collect the plasma, is connected on the one hand, at an inlet orifice 38, to the bag 21 by means of a tube 36 and on the other hand at an outlet orifice 41 to an inlet orifice 39 of the filter 13' by means of a tube 40.

The bag 35 is intended to receive the filtrate, that is to say the plasma with leukocytes removed. To this end, it is connected by means of a tube 42 and at an inlet orifice 43 to an outlet orifice 44 of the filter 13'.

This system makes it possible, after having been sterilised, to perform the following steps in closed circuit:
- respectively associating the filters 13 and 13' with the bags 1 and 35, by means of the temporary association means 8;
- collecting the whole blood in the primary bag 21;
- centrifuging the system so as to separate the blood into its components;
- disconnecting the filter 13 from the bag 1;
- collecting the high platelet content plasma in the satellite bag 30;
- filtering the erythrocyte concentrate and collecting the filtrate in the bag 1;
- centrifuging the system so as to separate the high platelet content plasma into a layer of platelets and a layer of plasma;
- disconnecting the filter 13' from the bag 35;
- filtering the plasma and collecting the filtrate in the bag 35.

According to one embodiment, the tubes 22, 25, 32, 36, 40 and 42 are separable and weldable so as to be able, after filtration, to separate the system from the bags containing a blood component and thus allow their possible subsequent transfusion.

In particular, prior to the second centrifugation, the part II and the bag 30 are disconnected from the system by cutting and welding the tube 32.

In embodiments which are not shown, the bag 1, 35 can be associated by means of a tube with another bag to allow subsequent treatment of the filtrate collected in the said bag 1, 35.

The invention claimed is:

1. A flexible bag assembly for receiving a biological fluid comprising:
   a flexible bag having an external enclosure formed by two sheets of flexible plastic connected at their periphery; and
   means disposed on the periphery of the external enclosure operable to allow temporary insertion of at least one component between the means and the external enclosure;
   wherein temporary insertion of the at least one component allows temporary association of the at least one component with the exterior of the flexible bag during centrifugation;
   and wherein the at least one component comprises a filter attached to the flexible bag by at least one tube.

2. The flexible bag of claim 1, wherein the filter comprises a flexible filter.

3. The flexible bag of claim 1, wherein temporary association of the at least one component with the flexible bag during centrifugation forms a compact assembly of the at least one component and the bag.

4. A bag system comprising:
   a flexible bag operable to contain a biological fluid and to be centrifuged and having an external enclosure;
   at least one flexible plastic member disposed on the external enclosure and operable to allow temporary insertion of at least one component between the plastic member and the external enclosure and not into an internal volume during centrifugation;
   and wherein the at least one component comprises a filter attached to the flexible bag by at least one tube.

5. The bag system of claim 4, wherein the at least one plastic member comprises at least one flexible strip of plastic disposed on the external enclosure to form a passage between the strip and the external enclosure.

6. The bag system of claim 5, wherein the flexible bag comprises a substantially rectangular bag.

7. The bag system of claim 4 where in the filter comprises a flexible filter.

8. The bag system of claim 4, wherein temporary association of the component with the flexible bag during centrifugation forms a compact assembly of the component and the bag.

9. The bag system of claim 4, further comprising the plastic member welded to the external enclosure of the bag.

10. A method of separating blood into constituent parts comprising:

providing blood in a flexible bag assembly having a flexible bag with an external enclosure and a plastic member disposed on the external enclosure and at least one additional component;

inserting the additional component between the external enclosure and the plastic member and not in an internal volume; and centrifuging the assembly to separate the blood into constituent parts;

removing the additional component from between the external enclosure and the plastic members;

and wherein the at least one additional component comprises a filter.

11. The method of claim 10, further comprising filtering a constituent part using the filter.

12. The method of claim 10, wherein inserting further comprises placing the additional component substantially in the center of a side of the external enclosure.

13. The method of claim 10, wherein the inserting step limits movement of the additional component with respect to the flexible bag during the centrifuging step.

* * * * *